United States Patent [19]
Cox, Jr.

[11] Patent Number: 4,944,750
[45] Date of Patent: Jul. 31, 1990

[54] COMPOSITE SHELL MATERIAL FOR PROSTHESIS

[75] Inventor: James E. Cox, Jr., Oxnard, Calif.

[73] Assignee: Cox-Uphoff International Reel, Carpinteria, Calif.

[21] Appl. No.: 256,659

[22] Filed: Oct. 12, 1988

[51] Int. Cl.$^5$ .............................................. A61F 2/12
[52] U.S. Cl. .......................................... 623/8; 428/16; 428/71; 428/314.4; 428/319.3; 428/447
[58] Field of Search ..................... 623/8; 128/165, 156; 428/16

[56] References Cited

U.S. PATENT DOCUMENTS

| | | | |
|---|---|---|---|
| 3,683,424 | 8/1972 | Pangman | 623/8 |
| 4,217,889 | 8/1980 | Radovan et al. | 623/8 |
| 4,455,691 | 6/1984 | Van Akenredinger et al. | 623/8 |
| 4,476,857 | 10/1984 | Levine | 128/165 |
| 4,773,409 | 9/1988 | Cilento et al. | 128/156 |

Primary Examiner—Richard J. Apley
Assistant Examiner—Stephanie L. Iantorno
Attorney, Agent, or Firm—Donald D. Mon

[57] ABSTRACT

An implantation prosthesis, and a composite material for use in constructing this prosthesis. The material is flexible. It has an inner wall, an outer wall, and a foam layer between the walls in adherent surface-to-surface contact. The walls are made of a flexible elastomeric material with at least limited permeability. The foam is resiliently deformable to resist sharp folding of the walls, and to resist relative in-plane motion of the walls.

5 Claims, 1 Drawing Sheet

COMPOSITE SHELL MATERIAL FOR PROSTHESIS

FIELD OF THE INVENTION

This invention relates to prostheses for the human body, and especially to mammary prostheses.

BACKGROUND OF THE INVENTION

Prostheses are wellknown for implantation in the body to replace removed tissue or to augment tissue already present. The objective is to provide a prothesis which will not be rejected by the body, and which after implantation will provide an improved visual configuration, and with it a tactile response which is close to that which arises from a normal body element, for example the female breast.

A well-known and generally successful prosthesis of this type has a relatively thin and quite flexible envelope made of vulcanized (cured) silicone elastomer. It is usually filled either with a silicone gel or with a normal saline solution. Because of the tendency of either of these fluids to pass through the envelope over a long period of time—even though it is an extremely slow process relating to limited semi-permeability, saline is preferred. Saline solutions do not adversely affect the tissues, while silicone gels can in some instances be troublesome.

As is so often the case, the improvement of one problem can give rise to another. A gel-filled prosthesis tends to hold its shape better than a saline filled envelope, assuming identical envelopes. This is in the sense of resisting tight bends and folds of the envelope material. Acceptably thin silicone envelopes are prone to splitting or to excess leakage if they are strongly folded. A saline solution provides little resistance to this folding, especially in comparison to an envelope filled with a gel where the gel, being more viscous, offers some resistance. Of course the tendency to break or to leak can be reduced by increasing the wall thickness of the envelope, but there comes a point where the gross properties of the prosthesis are then changed to an unacceptable degree, for example by an excessive loss of flexibilty which results in a structure that when palpated clearly includes a foreign structure. This deprives the patient of a very important advantage of a proper prosthesis.

Accordingly it is an object of this invention to provide a prosthesis to contain aqueous, usually saline, solutions, but which while retaining many of the textural and flexure properties of a conventional prosthesis, has a composite wall that is resistant to sharp folding.

BRIEF DESCRIPTION OF THE INVENTION

An envelope for a saline-filled or gel-filled prosthesis according to this invention comprises an inner wall and an outer wall, and between them and adherent to them, a stabilizing layer of foam material.

The dimensions and properties of this composite material are selected so as resiliently to resist in-plane shear motion of the walls, relative to one another, and to provide a resilient resistance to sharp crimping or folding motion, all while maintaining as nearly as possible the gross qualities of a suitable single-walled envelope.

DETAILED DESCRIPTION OF THE INVENTION

Figure 1:
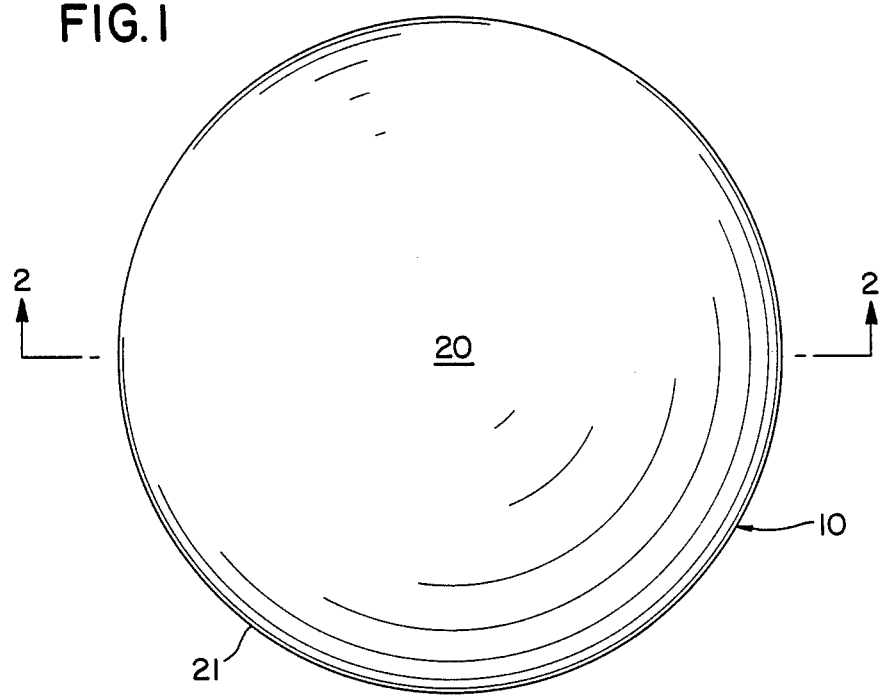
FIG. 1 is a top view of a mammary prosthesis according to the invention.
Figure 2:
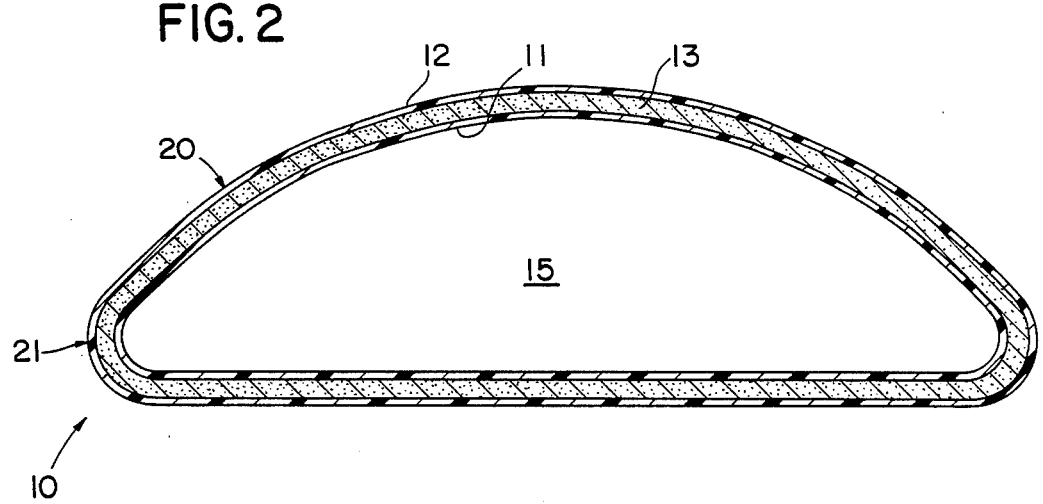
FIG. 2 is a cross-section taken at line 2—2 in FIG. 1.

A prosthesis 10 according to this invention is shown in the drawings. It comprises an inner wall 11 and an outer wall 12 which form all or most of the boundary of the prosthesis. A layer 13 of foam material is sandwiched between these walls. Layer 13 is cemented or otherwise adhered to both of these walls so it spaces them apart, and stays in place to provide resilient resistance to relative in-plane shear movement between the walls, and to be in resilient compressive opposition to forces which would tend to press them toward one another, or to bend them flexurally.

The envelope provides an internal cavity 15. Because of the advantages provided by the material of the envelope, normal saline solution will preferably be placed in the envelope to fill it to the volume desired, and also to generate the desired degree of firmness for the gross prosthesis. However, it is equally possible to fill the cavity with a gel such as silicone gel, or with any other fluid-like material or aqueous solution which can be tolerated by the body in the event of leakage.

Depending on the design of the prosthesis, its mode of implantation, and of possible later inflation or deflation, the prosthesis may or may not be equipped with valving means. Frequently the inflation and deflation can be accomplished with a trocar equipped syringe. Also, in many practical prostheses, the major part of the envelope is a continuous seamless structure, with a large aperture in its base which will bear against body structure such as the rib cage. It will be closed by a patch cemented to its margins. The material of this invention can be used for the patch, but need not be, because flexure does not occur in that region. Instead, the composite material will often be used only to form the dome portion 20, the rim portion 21, and such portions of the base as may be subject to flexure. These constitute the flexural part of the prosthesis. The remainder may be a simple patch of single-thickness material if preferred. It may be considerably simpler to provide this type of patch area with means such as valves for inflating or deflating the prosthesis.

The material of construction of the inner and outer walls may be of any suitable and known composition which is not rejected by the body. Medical grade silicone elastomer is a well-known example. A thickness on the order of 0.010 inches is suitable. The walls are continuous. While semi-permeable, they are not semi-permeable to an unacceptable extent, and satisfactorily form a fluid-containing envelope.

The foam need not be a silicone foam, and usually will not be. Instead, it will usually be made of some stronger, readily formed and biologically acceptable material such as polyurethane, about 50% density. Either a closed cell or an open cell foam may be used. Generally an open cell foam will be preferred, and over an extended period of time will be filled with fluid which has passed through the inner wall.

The foam layer will be cemented to both walls, using any suitable flexible cement of a type generally used in prostheses. The amount of cement used should be minimized so that it does not itself create a palpable layer.

Also, should an open-cell foam be used, least penetration into the foam layer is preferred in order not to rigidify the structure or excessively to close the cells at the foam surface.

However impermeable the material of the walls and of the foam, over a period of time the cells of the foam can be expected to fill up due to the osmotic pressures. However, normal saline has the advantage of minimal osmotic pressure differential across the walls, and leaking out of saline will be minimal.

The major, but not the only, advantage of this composite construction is that the foam resiliently resists relative inplane shear movement of the two walls, and provides an internal support that resists sharp folding of the walls which could break or weaken them, and thereby increase the risk of leakage. This is accomplished while still providing a prosthesis with acceptable gross properties as to firmness, flexibility and shape. As a further advantage, this enables normal saline solution to be used more reliably, because the fluid is not relied on to support the walls against folding. The folding forces to be resisted are those exerted as the consequence of normal body movements and usage. Palpation of the breasts, bouncing movements while jogging, and prone forces, are examples.

This invention is not to be limited by the embodiment shown in the drawings and described in the description, which is given by way of example and not of limitation, but only in accordance with the scope of the appended claims.

I claim:

1. A composite material to form a flexible part of an implantable prosthesis intended to contain a fluid, said material comprising: an inner wall, an outer wall, and a foam layer between said walls in adherent surface-to-surface contact therewith, both of said walls being made of a flexible elastomeric material which is impermeable or has limited permeability, and said foam being resiliently deformable to resist sharp folding of the walls and resiliently to resist relative in-plane motion of the walls.

2. A composite material according to claim 1 in which said foam layer is either open cell or closed cell foam.

3. A composite material according to claim 2 in which said walls are made of a vulcanized silicone elastomer, and said foam layer is made of polyurethane.

4. An implantable prosthesis having a base portion and a flexural portion, at least said flexural portion being made of a composite material according to claim 1, and forming a closed envelope with an internal cavity adapted to contain a fluid.

5. A prosthesis according to claim 4 in which said fluid is normal saline solution.

* * * * *